US00PP36811P2

(12) United States Plant Patent
Boxriker

(10) Patent No.: US PP36,811 P2
(45) Date of Patent: Jul. 8, 2025

(54) ***OSTEOSPERMUM* PLANT NAMED 'KLEOE23819'**

(50) Latin Name: ***Osteospermum ecklonis* Norl.**
Varietal Denomination: KLEOE23819

(71) Applicant: KLEMM + SOHN GMBH & CO. KG, Stuttgart (DE)

(72) Inventor: Maike Boxriker, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/779,369

(22) Filed: Jul. 22, 2024

(51) Int. Cl.
*A01H 5/02* (2018.01)
*A01H 6/14* (2018.01)

(52) U.S. Cl.
USPC ..... Plt./360

(58) Field of Classification Search
USPC ..... Plt./263.1, 360
See application file for complete search history.

(56) References Cited

U.S. PATENT DOCUMENTS

PP26,694 P3 * 5/2016 Brown ..... Plt./360
PP29,979 P2 * 12/2018 Klemm ..... Plt./360

* cited by examiner

*Primary Examiner* — Karen M Redden
(74) *Attorney, Agent, or Firm* — Weatherly IP Solutions, LLC; James M. Weatherly

(57) ABSTRACT

A new *Osteospermum* plant particularly distinguished by pink flowers with a white ring, with an upright habit, is disclosed.

1 Drawing Sheet

Genus and species: *Osteospermum ecklonis* Norl.
Variety denomination: 'KLEOE23819'.

BACKGROUND OF THE NEW PLANT

The present invention comprises a new and distinct variety of *Osteospermum*, botanically known as *Osteospermum ecklonis* Norl., and hereinafter referred to by the variety name 'KLEOE23819'. 'KLEOE23819' originated from a cross-pollination conducted in summer of 2020 in Nairobi, Kenya between the proprietary female *Osteospermum* variety 'OE-2018-5108' (unpatented) and the proprietary male *Osteospermum* variety 'OE-2018-5105' (unpatented).

The seeds from the cross were collected and sown in Stuttgart, Germany in January 2021 and the plants were grown for evaluation. An individual plant designated 'KLEOE23819' was selected in June 2021 in Stuttgart, Germany. In June 2021 'KLEOE23819' was first vegetatively propagated by vegetative terminal cuttings in Stuttgart, Germany. 'KLEOE23819' was found to reproduce true to type in successive generations of asexual propagation via vegetative cuttings.

SUMMARY

The following are the most outstanding and distinguishing characteristics of this new variety when grown under normal horticultural practices in Stuttgart, Germany.

1. Pink flowers with white ring; and
2. Upright habit.

DESCRIPTION OF THE PHOTOGRAPH

This new *Osteospermum* plant is illustrated by the accompanying photograph which shows a close-up of the foliage, buds, and mature flower. The photograph is of a 11-week-old plant grown indoors in Stuttgart, Germany in March 2023. The colors shown are as true as can be reasonably obtained by conventional photographic procedures.

DESCRIPTION OF THE NEW VARIETY

The following detailed descriptions set forth the distinctive characteristics of 'KLEOE23819'. The data which define these characteristics were collected in Stuttgart Germany in May 2024 on plants potted in October 2023. References are to The R.H.S. Colour Chart of The Royal Horticultural Society of London (R.H.S.), 5$^{th}$ edition (2007).

Classification:
- *Family.*—Asteraceae.
- *Botanical.*—*Osteospermum ecklonis* Norl.
- *Common.*—*Osteospermum.*
- *Designation.*—'KLEOE23819'.

Parentage:
- *Female parent.*—The proprietary female *Osteospermum* variety 'OE-2018-5108' (unpatented).
- *Male parent.*—The proprietary male *Osteospermum* variety 'OE-2018-5105' (unpatented).

Plant:
- *Form and habit.*—Herbaceous perennial but usually cultivated as an annual; not frost resistant.
- *Growth habit.*—Upright.
- *Branching habit.*—Normal.
- *Height (from top of soil, including inflorescence).*—13.0 cm.
- *Width (including inflorescences).*—16.0 cm.
- *Propagation.*—Vegetative cuttings.
- *Time to produce a finished flowering plant.*—10 to 17 weeks.
- *Time to initiate and develop roots.*—4 weeks.
- *Root description.*—Fine; RHS 155A (white).

Leaves:
*Arrangement*.—Alternate.
*Shape*.—Obovate.
*Apex*.—Acute.
*Base*.—Acute.
*Margin*.—Entire.
*Immature color*.—Upper surface: RHS 137C. Lower surface: RHS 137A.
*Mature color*.—Upper surface: RHS N137A. Lower surface: RHS 138A.
*Length*.—3.4 cm.
*Width*.—1.9 cm.
*Texture*.—Upper surface: Leathery. Lower surface: Leathery with fine hairs.
*Petioles*.—Absent.
*Venation pattern*.—Pinnate.
*Venation color*.—Upper surface: RHS N137A. Lower surface: RHS 138A.

Stems:
*Total number of branches per plant* (*calculated at the base of the plant*).—3.
*Length*.—13.0 cm.
*Diameter*.—0.2 cm.
*Internode length*.—1.8 cm.
*Color*.—RHS 15A.
*Texture*.—Smooth.
*Anthocyanin*.—RHS N77D.

Buds:
*Shape*.—Round.
*Length*.—0.8 cm.
*Diameter*.—0.8 cm.
*Color* (*at tight bud just before the ray florets unfold*).—RHS 146A.

Inflorescence:
*Type*.—Composite, single.
*Blooming habit*.—Upright, with longer flower stems.
*Quantity of inflorescences per plant*.—12.
*Lastingness of the inflorescences on the plant*.—10 to 15 days.
*Fragrance*.—Present.
*Inflorescence diameter*.—6.3 cm.
*Inflorescence depth*.—1.5 cm.
*Disc diameter*.—1.3 cm.

Disc floret:
*Quantity per inflorescence*.—Around 50.
*Shape*.—Tubular.
*Tube color*.—Closed: RHS 155C. Mature: RHS 155C.
*Length*.—0.5 cm.
*Diameter* (*at apex*).—0.1 cm.
*Apex*.—Acute.
*Apex color*.—RHS N88B.
*Base*.—Acute.
*Base color*.—RHS 145D.
*Margin*.—Entire.

Ray floret:
*Quantity per inflorescence*.—24.
*Shape*.—Oblanceolate.
*Color*.—Upper surface: RHS 76D (light pink) base with 75A darker pink coloring toward the apex forming a basal ring. Lower surface: RHS 84D.
*Length*.—3.3 cm.
*Width*.—0.8 cm.
*Apex*.—Obtuse.
*Base*.—Acute.
*Margin*.—Entire.
*Texture*.—Upper surface: Smooth. Lower surface: Smooth.
*Peduncle*.—Length: 3.8 cm. Diameter: 0.2 cm. Texture: Smooth with hairs. Color: RHS 144C.

Phyllaries:
*Texture*.—Smooth with fine hairs.
*Color*.—RHS 138A.
Arrangement.—Single.
*Observed quantity per plant*.—21.
*Shape*.—Lanceolate.
*Color*.—Upper surface: RHS 138A. Lower surface: RHS 145A.
*Length*.—1.0 cm.
*Width*.—0.2 cm.
*Apex*.—Acute.
*Base*.—Obtuse.
*Margin*.—Entire.
*Texture*.—Upper surface: Smooth with fine hairs. Lower surface: Smooth.

Reproductive organs:
*Androecium*.—Location: On the disc floret. Stamens: Quantity: Numerous. Shape: Filamentous. Filament length: 0.4 cm. Filament diameter: Less than 0.1 cm. Anther: Shape: Lanceolate. Color: RHS N77A. Length: 0.5 cm. Diameter: 0.1 cm. Pollen: Color: RHS 17A. Amount: Abundant.
*Gynoecium*.—Location: On the base of the petals (ray floret). Pistils: Number: Numerous. Length: 0.3 cm. Diameter: Less than 0.1 cm. Stigma: Color: RHS 79A. Shape: Filamentous. Length: 0.2 cm. Diameter: Less than 0.1 cm. Style: Color: RHS 79A. Length: 0.1 cm. Diameter: Less than 0.1 cm.

Fruit and seed set: None observed.

Disease and pest/insect resistance: No disease and pest/insect resistance observed.

COMPARISON WITH PARENTAL LINES AND KNOWN VARIETY

'KLEOE23819' is a distinct variety of *Osteospermum* and is distinguished from its parents as described in Table 1.

TABLE 1

Comparison with Parental Lines

| Characteristic | 'KLEOE23819' | Female Parent | Male Parent |
|---|---|---|---|
| Flower color | Pink with white ring | Pink with white ring | Pink with white ring |
| Expression of white ring | Better expression than the female and the male parents | Less expression than 'KLEOE23819' | Less expression than 'KLEOE23819' |
| Compact | More compact than female and male parents | Less compact than 'KLEOE23819' | Less compact than 'KLEOE23819' |

'KLEOE23819' is most similar to the commercial *Osteospermum* variety 'KLEOE23094' (unpatented). Differences between the varieties are described in Table 2.

TABLE 2

Comparison with Similar Variety

| Characteristic | 'KLEOE23819' | 'KLEOE23094' |
|---|---|---|
| Flower color | Pink with white ring | Purple |
| Branching | Good | Strong |

I claim:

1. A new and distinct cultivar of *Osteospermum* Plant Named 'KLEOE23819' as illustrated and described herein.

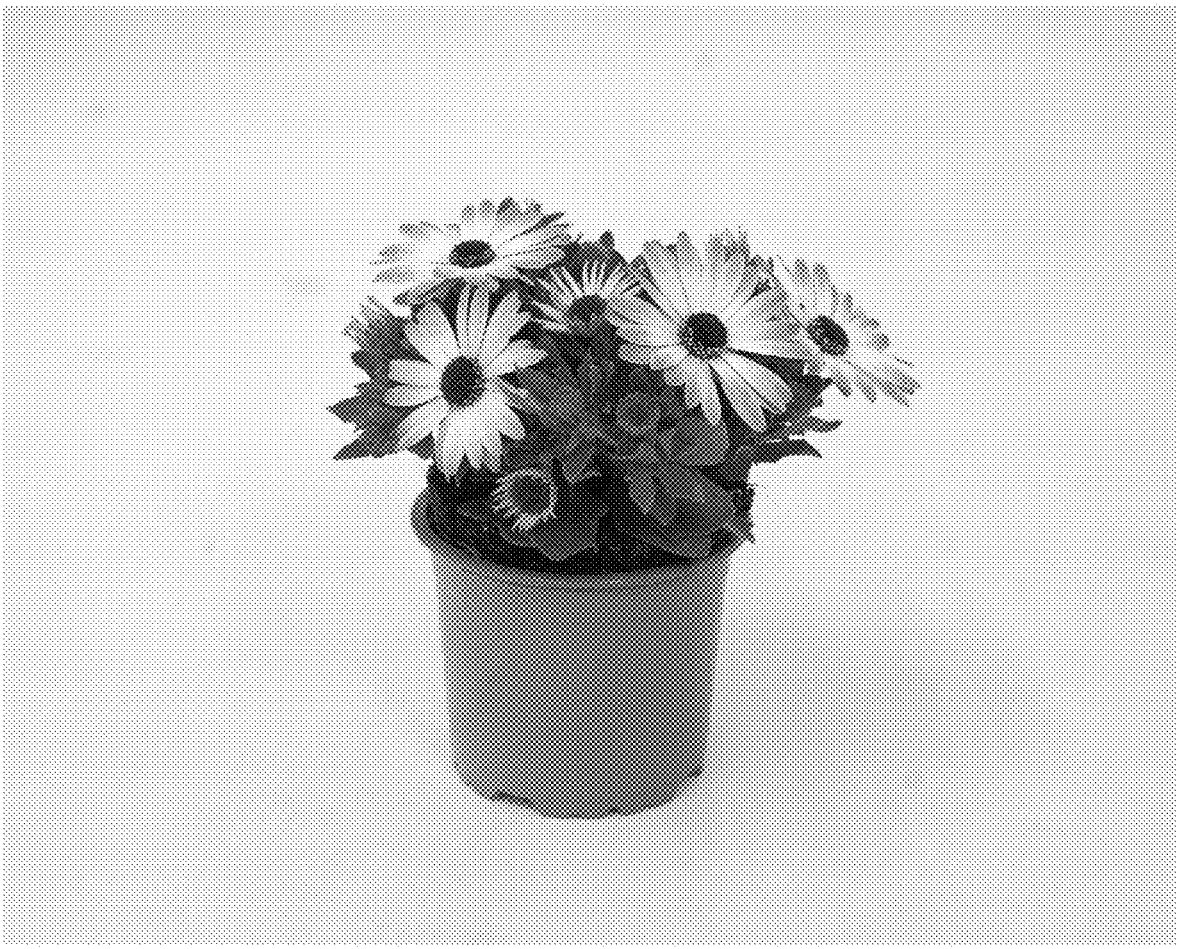

* * * * *